(12) United States Patent
Kotzian

(10) Patent No.: US 7,338,920 B2
(45) Date of Patent: Mar. 4, 2008

(54) HERBICIDAL COMPOSITION

(75) Inventor: Georg Rüdiger Kotzian, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 156 days.

(21) Appl. No.: 10/491,266

(22) PCT Filed: Oct. 4, 2002

(86) PCT No.: PCT/EP02/11143

§ 371 (c)(1),
(2), (4) Date: Mar. 29, 2004

(87) PCT Pub. No.: WO03/030641

PCT Pub. Date: Apr. 17, 2003

(65) Prior Publication Data

US 2004/0242420 A1    Dec. 2, 2004

(30) Foreign Application Priority Data

Oct. 5, 2001    (CH) .................................. 1837/01

(51) Int. Cl.
*A01N 37/18*    (2006.01)
(52) U.S. Cl. ..................... 504/149; 504/105
(58) Field of Classification Search ............... 504/129, 504/130, 133, 136, 139, 140, 143, 149
See application file for complete search history.

(56) References Cited

U.S. PATENT DOCUMENTS

| 4,168,965 A | * | 9/1979 | Vogel et al. | ................ | 504/342 |
| 5,650,373 A | * | 7/1997 | Ort et al. | ................ | 504/127 |
| 5,928,997 A | * | 7/1999 | Bauer et al. | ................ | 504/133 |

FOREIGN PATENT DOCUMENTS

| CH | 651445 | 9/1985 |
| CN | 1286907 | 3/2001 |
| CN | 1286909 | 3/2001 |
| DE | 4209475 | 9/1993 |
| DE | 19834627 | 12/1998 |
| WO | 9105469 | 5/1991 |
| WO | 9703562 | 2/1997 |
| WO | 02100173 | 12/2002 |

OTHER PUBLICATIONS

"The Pesticide Manual" 2000, British Crop Protection Council, p. 386-387.
Database WPI Section Ch, Week 200153, Derwent Publciations Ltd., London, GB; Class C03, AN 2001-483738 & CN 1 286 907 A (Tongzhou City Plant Hospital), Mar. 14, 2001; abstract.

* cited by examiner

*Primary Examiner*—Neil S. Levy
(74) *Attorney, Agent, or Firm*—Rebecca A. Howard

(57) ABSTRACT

Herbicidal composition which, in addition to comprising customary inert formulation adjuvants, comprises a) the compound of formula I (I), and b) a synergistically effective amount of one or more co-herbicides selected from the group consisting of the co-herbicides: paraquat (592), mesotrione (500), sulcotrione (710), clomazone (159), fentrazamide (340), mefenacet (491), oxaziclomefone (583), indanofan (450), glyphosate (407), prosulfocarb (656), molinate (542), triasulfuron (773) and halosulfuron-methyl (414), with the exception of active ingredient combinations consisting of compound of formula I+mefenacet, compound of formula I+clomazone and compound of formula I+glyphosate. The compositions according to the invention may also comprise a safener.

(I)

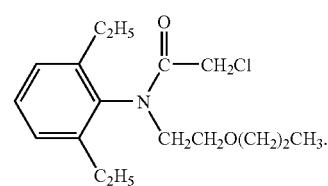

9 Claims, No Drawings

HERBICIDAL COMPOSITION

The present invention relates to a novel herbicidal composition comprising a herbicidal active ingredient combination that is suitable for selective weed control in crops of useful plants, for example in crops of rice.

The invention relates also to a method of controlling weeds in crops of useful plants, comprising the herbicidal composition, and to the use of the novel composition for that purpose.

Compound a) 2-chloro-N-(2,6-diethylphenyl)-N-(2-propoxyethyl)acetamide of formula I

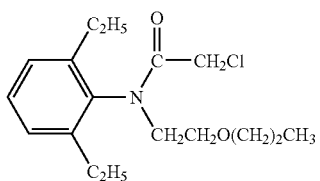

exhibits herbicidal activity, as is described, for example, in GB-A-1 438 311 and GB-A-1 438 312.

Surprisingly, it has now been found that a combination of variable amounts of active ingredients, that is to say a combination of a compound of formula I under a) with one or more of the herbicidal active ingredients listed below under b), all of which are known and some of which are also available commercially, develops a synergistic action that is capable of controlling, both pre-emergence and post-emergence, the majority of the weeds and grasses occurring especially in crops of useful plants, without causing any appreciable damage to the useful plant.

There is therefore proposed according to the present invention a novel synergistic composition for selective weed control which, in addition to comprising customary inert formulation adjuvants, comprises as active ingredient a mixture of a) a herbicidally effective amount of the compound of formula I

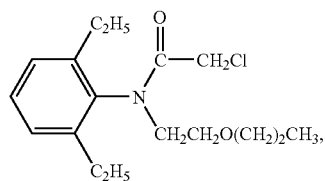

and b) a synergistically effective amount of one or more compounds selected from the group consisting of the co-herbicides: paraquat (592), mesotrione (500), sulcotrione (710), clomazone (159), fentrazamide (340), mefenacet (491), oxaziclomefone (583), indanofan (450), glyphosate (407), prosulfocarb (656), molinate (542), triasulfuron (773) and halosulfuron-methyl (414), with the exception of the active ingredient combinations consisting of compound of formula I+mefenacet, compound of formula I+clomazone and compound of formula I+glyphosate.

The compound of formula I is known as a herbicide by the common name pretilachlor and is described, for example, in "The Pesticide Manual", Editor C. D. S. Tomlin, 12th Edition, British Crop Protection Council, 2000, under entry number (632) and is registered under CAS-Reg. No. [5121-849-6].

The above herbicidal active ingredients under b) are known and described, for example, in "The Pesticide Manual", Editor C. D. S. Tomlin, 12th Edition, British Crop Protection Council, 2000, under the entry numbers added in brackets; for example, mesotrione (500) is described therein under entry number 500.

The following specific active ingredient combinations have proved to be especially effective synergistic compositions: compound of formula I+paraquat; compound of formula I+fentrazamide; compound of formula I+mesotrione; compound of formula I+sulcotrione; compound of formula I+oxaziclomefone; compound of formula I+indanofan; compound of formula I+molinate; compound of formula I+prosulfocarb; compound of formula I+triasulfuron; and compound of formula I+halosulfuron-methyl.

Synergistic compositions that are also especially effective comprise the following specific active ingredient combinations: compound of formula I+molinate+triasulfuron; compound of formula I+molinate+mesotrione; compound of formula I+molinate+halosulfuron-methyl; compound of formula I+mesotrione+triasulfuron; and compound of formula I+mesotrione+halosulfuron-methyl.

It is extremely surprising that the combination of the active ingredient of formula I under a) with one or more active ingredients selected from the co-herbicides under b) exceeds the additive action on the weeds to be controlled that is to be expected in principle and thus broadens the range of action of the individual active ingredients especially in two respects: firstly, the rates of application of the individual compounds of formula I under a) and co-herbicides under b) are reduced while a good level of action is maintained and, secondly, the composition according to the invention achieves a high level of weed control also in those cases where the individual substances, in the range of low rates of application, have become useless from the agronomic standpoint. The result is a considerable broadening of the spectrum of weeds and an additional increase in selectivity in respect of the crops of useful plants, as is necessary and desirable in the event of an unintentional overdose of active ingredient. The composition according to the invention, while retaining excellent control of weeds in crops of useful plants, also allows greater flexibility in succeeding crops.

The composition according to the invention can be used against a large number of agronomically important weeds, such as *Eleocaris, Nasturtium, Ludwigia* spp., *Digitaria, Lindernia* spp., *Setaria, Fimbristylis, Leptochloa, Solanum, Phaseolus, Echinochloa, Scirpus, Monochoria, Sagittaria, Alopecurus, Sorghum halepense, Rottboellia, Cyperus, Abutilon, Sida, Xanthium, Ipomoea* and *Chrysanthemum*. The composition according to the invention is suitable for all methods of application conventionally used in agriculture, for example pre-emergence application, post-emergence application and seed dressing. The composition according to the invention is suitable especially for controlling weeds in crops of useful plants, such as rice.

"Crops" are to be understood to mean also those crops which have been made tolerant to herbicides or classes of herbicides as a result of conventional methods of breeding or genetic engineering.

The composition according to the invention comprises the compound of formula I under a) and the co-herbicides under b) in any desired mixing ratio, usually with an excess of one component over the other. Generally, the mixing ratios (ratios by weight) of the compound of formula I and the co-herbicides under b) are from 1:2000 to 2000:1, especially from 200:1 to 1:200.

The rate of application may vary within wide limits and depends on the nature of the soil, the method of application (pre- or post-emergence; seed dressing; application to the seed furrow; no tillage application etc.), the crop plant, the weed to be controlled, the prevailing climatic conditions, and other factors governed by the method of application, the time of application and the target crop. The active ingredient mixture according to the invention can generally be applied at a rate of from 1 to 5000 g/ha, especially from 1 to 2000 g of active ingredient mixture/ha.

The invention relates also to a method of selectively controlling weeds and grasses in crops of useful plants, which comprises treating the useful plants, seeds or cuttings thereof or the area of cultivation thereof, simultaneously or separately, with an amount, effective for herbicide synergy, of the herbicide a) and at least one further co-herbicide b). Preference is given to a method which comprises applying the herbicide a) to the useful plants, especially rice, or to the locus of the useful plants, and applying a further co-herbicide b), or optionally a mixture of those substances, together with the herbicide a) or at a later date. The same active ingredients as listed above are suitable as the herbicide a) and co-herbicides b).

The mixtures of the compound of formula I under a) with the co-herbicides under b) may be used in unmodified form, that is to say as obtained in synthesis. Preferably, however, they are formulated in customary manner, together with the adjuvants conventionally employed in formulation technology, such as solvents, solid carriers or surfactants, for example into emulsifiable concentrates, directly sprayable or dilutable solutions, dilute emulsions, wettable powders, soluble powders, dusts, granules or microcapsules, as is described on pages 9 to 13 of WO 97/34483. As with the nature of the compositions, the methods of application, such as spraying, atomising, dusting, wetting, scattering or pouring, are chosen in accordance with the intended objectives and the prevailing circumstances.

The formulations, that is to say the compositions, preparations or mixtures comprising the compound of formula I under a) and the co-herbicides under b) and, optionally, one or more solid or liquid formulation adjuvants, are prepared in known manner, e.g. by intimately mixing and/or grinding the active ingredients with the formulation adjuvants, for example solvents or solid carriers. Surface-active compounds (surfactants) may additionally also be used in the preparation of the formulations.

Examples of solvents and solid carriers are given, for example, on page 6 of WO 97/34485.

Depending on the nature of the compound of formula I and the co-herbicides under b) to be formulated, suitable surface-active compounds are non-ionic, cationic and/or anionic surfactants and surfactant mixtures having good emulsifying, dispersing and wetting properties.

Examples of suitable anionic, non-ionic and cationic surfactants are listed, for example, on pages 7 and 8 of WO 97/34485.

Also suitable for the preparation of the herbicidal compositions according to the invention are the surfactants conventionally employed in formulation technology, which are described, inter alia, in "McCutcheon's Detergents and Emulsifiers Annual" MC Publishing Corp., Ridgewood N.J., 1981, Stache, H., "Tensid-Taschenbuch", Carl Hanser Verlag, Munich/Vienna, 1981 and M. and J. Ash, "Encyclopedia of Surfactants", Vol. I-III, Chemical Publishing Co., N.Y., 1980-81.

The herbicidal formulations usually comprise from 0.1 to 99% by weight, especially from 0.1 to 95% by weight, of active ingredient mixture comprising the compound of formula I together with the co-herbicides under b), from 1 to 99.9% by weight of a solid or liquid formulation adjuvant, and from 0 to 25% by weight, especially from 0.1 to 25% by weight, of a surfactant.

Whereas commercial products will preferably be formulated as concentrates, the end user will normally employ dilute formulations. The compositions may also comprise further additives, such as stabilisers, for example vegetable oils or epoxidised vegetable oils (epoxidised coconut oil, rapeseed oil or soybean oil), anti-foams, for example silicone oil, preservatives, viscosity regulators, binders, tackifiers, and also fertilisers or other active ingredients. Preferred formulations have especially the following compositions:

(%=percent by weight)

Emulsifiable Concentrates:
  active ingredient mixture: 1 to 90%, preferably 5 to 20%
  surfactant: 1 to 30%, preferably 10 to 20%
  liquid carrier: 5 to 94%, preferably 70 to 85%

Dusts:
  active ingredient mixture: 0.1 to 10%, preferably 0.1 to 5%
  solid carrier: 99.9 to 90%, preferably 99.9 to 99%

Suspension Concentrates:
  active ingredient mixture: 5 to 75%, preferably 10 to 50%
  water: 94 to 24%, preferably 88 to 30%
  surfactant: 1 to 40%, preferably 2 to 30%

Wettable Powders:
  active ingredient mixture: 0.5 to 90%, preferably 1 to 80%
  surfactant: 0.5 to 20%, preferably 1 to 15%
  solid carrier: 5 to 95%, preferably 15 to 90%

Granules:
  active ingredient mixture: 0.1 to 30%, preferably 0.1 to 15%
  solid carrier: 99.5 to 70%, preferably 97 to 85%

The following Examples further illustrate but do not limit the invention.

| F1. Emulsifiable concentrates | a) | b) | c) | d) |
|---|---|---|---|---|
| active ingredient mixture | 5% | 10% | 25% | 50% |
| calcium dodecylbenzenesulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| cyclohexanone | — | — | 10% | 20% |
| arom. hydrocarbon mixture $C_9$-$C_{12}$ | 85% | 78% | 55% | 16% |

Emulsions of any desired concentration can be obtained from such concentrates by dilution with water.

| F2. Solutions | a) | b) | c) | d) |
|---|---|---|---|---|
| active ingredient mixture | 5% | 10% | 50% | 90% |
| 1-methoxy-3-(3-methoxy-propoxy)-propane | — | 20% | 20% | — |
| polyethylene glycol MW 400 | 20% | 10% | — | — |
| N-methyl-2-pyrrolidone | — | — | 30% | 10% |
| arom. hydrocarbon mixture $C_9$-$C_{12}$ | 75% | 60% | — | — |

The solutions are suitable for use in the form of microdrops.

| F3. Wettable powders | a) | b) | c) | d) |
|---|---|---|---|---|
| active ingredient mixture | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly dispersed silicic acid | 1% | 3% | 5% | 10% |
| kaolin | 88% | 62% | 35% | — |

The active ingredient (or active ingredient mixture) is mixed thoroughly with the adjuvants and the mixture is thoroughly ground in a suitable mill, affording wettable powders which can be diluted with water to give suspensions of any desired concentration.

| F4. Coated granules | a) | b) | c) |
|---|---|---|---|
| active ingredient mixture | 0.1% | 5% | 15% |
| highly dispersed silicic acid | 0.9% | 2% | 2% |
| inorganic carrier (diameter 0.1-1 mm) e.g. CaCO$_3$ or SiO$_2$ | 99.0% | 93% | 83% |

The active ingredient (or active ingredient mixture) is dissolved in methylene chloride and applied to the carrier by spraying, and the solvent is then evaporated off in vacuo.

| F5. Coated granules | a) | b) | c) |
|---|---|---|---|
| active ingredient mixture | 0.1% | 5% | 15% |
| polyethylene glycol MW 200 | 1.0% | 2% | 3% |
| highly dispersed silicic acid | 0.9% | 1% | 2% |
| inorganic carrier (diameter 0.1-1 mm) e.g. CaCO$_3$ or SiO$_2$ | 98.0% | 92% | 80% |

The finely ground active ingredient (or active ingredient mixture) is uniformly applied, in a mixer, to the carrier moistened with polyethylene glycol. Non-dusty coated granules are obtained in this manner.

| F6. Extruder granules | a) | b) | c) | d) |
|---|---|---|---|---|
| active ingredient mixture | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredients (or active ingredient mixture) are mixed and ground with the adjuvants, and the mixture is moistened with water. The mixture is extruded and then dried in a stream of air.

| F7. Dusts | a) | b) | c) |
|---|---|---|---|
| active ingredient mixture | 0.1% | 1% | 5% |
| talcum | 39.9% | 49% | 35% |
| kaolin | 60.0% | 50% | 60% |

Ready-to-use dusts are obtained by mixing the active ingredients (or active ingredient mixture) with the carriers and grinding the mixture in a suitable mill.

| F8. Suspension concentrates | a) | b) | c) | d) |
|---|---|---|---|---|
| active ingredient mixture | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredients (or active ingredient mixture) are intimately mixed with the adjuvants, giving a suspension concentrate from which suspensions of any desired concentration can be obtained by dilution with water.

It is often more practical for the compound of formula I and the mixing partner or partners under b) to be formulated separately and then to be brought together in the desired mixing ratio in the applicator in the form of a "tank mixture" in water shortly before application.

BIOLOGICAL EXAMPLES

A synergistic effect exists whenever the action of the active ingredient combination of compound of formula I and co-herbicides under b) is greater than the sum of the actions of the active ingredients applied separately.

The herbicidal action to be expected We for a given combination of two herbicides can be calculated as follows (see COLBY, S. R., "Calculating synergistic and antagonistic response of herbicide combinations", Weeds 15, pages 20-22, 1967):

$$We = X + [Y \cdot (100-X)/100]$$

wherein:

X=percentage herbicidal action on treatment with the compound of formula I at a rate of application of p kg per hectare, compared with the untreated control (=0%).

Y=percentage herbicidal action on treatment with a co-herbicide under b) at a rate of application of q kg per hectare, compared with the untreated control.

We=expected herbicidal action (percentage herbicidal action compared with the untreated control) following treatment with compound of formula I under a) and co-herbicide under b) at a rate of application of p+q kg of active ingredient per hectare.

When the action actually observed is greater than the value to be expected We, there is a synergistic effect.

The synergistic effect of the combinations of the compound of formula I under a) with the co-herbicides under b) is demonstrated in the following Examples.

EXAMPLE B1

Experiment Description—Pre-emergence Test

Monocotyledonous and dicotyledonous test plants are sown in standard soil in plastics pots. Directly after sowing, the test compounds are applied to the soil surface by spraying, both on their own and as a mixture. The test compounds are applied in the form of an aqueous suspension prepared from a 25% suspension concentrate (Example F8, c)) with 500 litres of water/ha. The rates of application depend on the optimum concentrations ascertained under field conditions or greenhouse conditions. The test plants are then grown on in a greenhouse under optimum conditions. The tests are evaluated after 1 to 4 weeks (% action, 100%=plant has died, 0%=no phytotoxic action).

The mixtures used in this test exhibit good synergistic effects.

EXAMPLE B2

Experiment Description—Post-emergence Test

The test plants are grown to the 1- to 3-leaf stage in plastics pots under greenhouse conditions. A standard soil is used as cultivation substrate. At the 1- to 3-leaf stage, the herbicides are applied to the test plants on their own and as a mixture. The test compounds are applied in the form of an aqueous suspension prepared from a 25% suspension concentrate (Example F8, c)) with 500 litres of water/ha. The rates of application depend on the optimum concentrations ascertained under field conditions or greenhouse conditions. The tests are evaluated after 1 to 4 weeks (% action, 100%=plant has died, 0%=no phytotoxic action).

The mixtures used in this test exhibit good synergistic effects.

It has been shown, surprisingly, that particular safeners are suitable for mixing with the synergistic composition according to the invention. The present invention accordingly relates also to a selectively herbicidal composition for controlling grasses and weeds in crops of useful plants, especially in crops of rice, which comprises a compound of formula I under a), one or more compounds selected from the co-herbicides under b), and a safener (counter-agent, antidote) and which protects the useful plants, but not the weeds, against the phytotoxic action of the herbicide, as well as to the use of such a composition in the control of weeds in crops of useful plants.

There is accordingly also proposed according to the invention a selectively herbicidal composition which, in addition to comprising customary inert formulation adjuvants, such as carriers, solvents and wetting agents, comprises as active ingredient a mixture of ab) an amount, effective for herbicide synergy, of the compound of formula I under a) and one or more compounds selected from the co-herbicides under b), and c) an amount, effective for herbicide antagonism, of the compound of formula 3.1

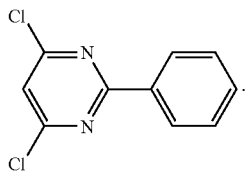

(3.1)

The compound of formula 3.1 is known as a herbicide by the common name fenclorim and is described, for example, in "The Pesticide Manual", 12th Edition, British Crop Protection Council, 2000, under entry number (325).

Preferred selective compositions according to the invention comprise as safener the compound of formula 3.1 in combination with the synergistic compositions described above as being especially effective and comprising the compound of formula I and one or more compounds selected from the group consisting of the co-herbicides under b).

Especially preferred selective compositions comprise the following specific active ingredient combinations: compound of formula I+molinate+triasulfuron+fenclorim; compound of formula I+molinate+mesotrione+fenclorim; compound of formula I+molinate+halosulfuron-methyl+fenclorim; compound of formula I+mesotrione+triasulfuron+fenclorim; and compound of formula I+mesotrione+halosulfuron-methyl+fenclorim.

The invention relates also to a method for the selective control of weeds in crops of useful plants, which comprises treating the useful plants, seeds or cuttings thereof, or the area of cultivation thereof, with a herbicidally effective amount ab) of the herbicide of formula I and one or more herbicides selected from the co-herbicides under b), and an amount, effective for herbicide antagonism, of the safener under c) of formula 3.1.

As crop plants that can be protected by the safener of formula 3.1 against the damaging effect of the above-mentioned herbicides there come into consideration especially rice. "Crops" are to be understood to mean also those crops which have been made tolerant to herbicides or classes of herbicides as a result of conventional methods of breeding or genetic engineering.

The weeds to be controlled may be both monocotyledonous and dicotyledonous weeds, for example *Eleocaris, Nasturtium, Ludwigia spp., Digitaria, Lindemia spp., Setaria, Fimbristylis, Leptochloa, Solanum, Phaseolus, Echinochloa, Scirpus, Monochoria, Sagittaria, Alopecurus, Sorghum halepense, Rottboellia, Cyperus, Abutilon, Sida, Xanthium, Ipomoea* and *Chrysanthemum*.

Areas of cultivation include the areas of ground on which the crop plants are already growing or which have already been sown with the seeds of those crop plants, as well as ground intended for cultivation with such crop plants.

Depending on the intended use, the safener of formula 3.1 can be used to pretreat the seed of the crop plant (dressing of the seeds or cuttings) or can be introduced into the soil before or after sowing. It can, however, also be applied alone or together with the herbicide after emergence of the plants. The treatment of the plants or seeds with the safener can therefore in principle be carried out independently of the time at which the herbicide is applied. The plants can, however, also be treated by simultaneous application of herbicide and safener (e.g. in the form of a tank mixture). The ratio of the rate of application of safener to the rate of application of herbicide depends largely on the method of application. In the case of field treatment, which is carried out either using a tank mixture comprising a combination of safener and herbicide or by separate application of safener and herbicide, the ratio of herbicides to safener is generally from 100:1 to 1:10, preferably from 20:1 to 1:1. In the case of field treatment it is usual to apply from 1 to 1000 g of safener/ha, preferably from 1 to 250 g of safener/ha.

The rate of application of herbicides is generally from 1 to 5000 g/ha, but preferably from 1 to 2000 g/ha.

The compositions according to the invention are suitable for all methods of application conventionally used in agriculture, for example pre-emergence application, post-emergence application and seed dressing.

In the case of seed dressing, generally from 0.001 to 10 g of safener/kg of seed, preferably from 0.05 to 2 g of safener/kg of seed, are applied. When the safener is applied in liquid form shortly before sowing, with soaking of the seeds, then there are advantageously used safener solutions that comprise the active ingredient in a concentration of from 1 to 10 000 ppm, preferably from 100 to 1000 ppm.

For the purpose of application, the safener of formula 3.1 with ab) the herbicide of formula I and one or more herbicides selected from the co-herbicides under b) are advantageously formulated together with the adjuvants conventionally employed in formulation technology, e.g. into emulsifiable concentrates, coatable pastes, directly sprayable or dilutable solutions, dilute emulsions, wettable powders, soluble powders, dusts, granules or microcapsules.

Such formulations are described, for example, on pages 9 to 13 of WO 97/34485. The formulations are prepared in known manner, e.g. by intimately mixing and/or grinding the active ingredients with liquid or solid formulation adjuvants, e.g. solvents or solid carriers. Surface-active compounds (surfactants) can additionally also be used in the preparation of the formulations. Solvents and solid carriers suitable for that purpose are mentioned, for example, on page 6 of WO 97/34485.

Depending on the nature of the active ingredient ab) of formula I and co-herbicides under b) and safener under c) of formula 3.1 to be formulated, suitable surface-active compounds are non-ionic, cationic and/or anionic surfactants and surfactant mixtures having good emulsifying, dispersing and wetting properties. Examples of suitable anionic, non-ionic and cationic surfactants are listed, for example, on pages 7 and 8 of WO 97/34485. Also suitable for the preparation of the herbicidal compositions according to the invention are the surfactants conventionally employed in formulation technology, which are described, inter alia, in "McCutcheon's Detergents and Emulsifiers Annual" MC Publishing Corp., Ridgewood N.J., 1981, Stache, H., "Tensid-Taschenbuch", Carl HanserVerlag, Munich/Vienna, 1981 and M. and J. Ash, "Encyclopedia of Surfactants", Vol. I-III, Chemical Publishing Co., New York, 1980-81.

The herbicidal formulations usually comprise from 0.1 to 99% by weight, especially from 0.1 to 95% by weight, of active ingredient mixture comprising ab) the compound of formula 1, and at least one compound selected from the co-herbicides under b), and the safener under c) of formula 3.1, from 1 to 99.9% by weight of a solid or liquid formulation adjuvant and from 0 to 25% by weight, especially from 0.1 to 25% by weight, of a surfactant. Whereas commercial products will preferably be formulated as concentrates, the end user will normally employ dilute formulations.

The compositions may also comprise further additives, such as stabilisers, for example vegetable oils or epoxidised vegetable oils (epoxidised coconut oil, rapeseed oil or soybean oil), anti-foams, e.g. silicone oil, preservatives, viscosity regulators, binders, tackifiers, and also fertilisers or other active ingredients. For the use of the safener under c) of formula 3.1, or of compositions comprising it, in the protection of crop plants against the damaging effects of ab) herbicides of formula I and co-herbicides under b), various methods and techniques come into consideration, such as, for example, the following:

i) Seed Dressing a) Dressing of the seeds with a wettable powder formulation of the compound of formula 3.1 by shaking in a vessel until uniformly distributed over the seed surface (dry dressing). In that procedure approximately from 1 to 500 g of compound of formula 3.1 (4 g to 2 kg of wettable powder) are used per 100 kg of seed.

b) Dressing of the seeds with an emulsifiable concentrate of the compound of formula 3.1 according to method a) (wet dressing).

c) Dressing by immersing the seeds for from 1 to 72 hours in a liquor comprising from 100 to 1000 ppm of the compound of formula 3.1 and optionally subsequently drying the seeds (immersion dressing).

Dressing the seed or treating the germinated seedling are naturally the preferred methods of application, because treatment with the active ingredients is directed entirely at the target crop. Generally from 1 to 1000 g of antidote, preferably from 5 to 250 g of antidote, are used per 100 kg of seed, but depending on the methodology, which also allows other active ingredients or micronutrients to be added, concentrations above or below the limits indicated may be employed (repeat dressing).

ii) Application as a Tank Mixture

A liquid formulation of a mixture of antidote and herbicide is used (ratio by weight of the one to the other from 10:1 to 1:100), the rate of application of herbicide being from 0.005 to 5.0 kg per hectare. Such tank mixtures are applied before or after sowing.

iii) Application to the Seed Furrow

The compound of formula 3.1 is introduced into the open, sown seed furrow in the form of an emulsifiable concentrate, wettable powder or granules. Once the seed furrow has been covered over, the herbicide is applied in the usual manner pre-emergence.

iv) Controlled Release of Active Ingredient

The compound of formula 3.1 is applied in solution to mineral granule carriers or polymerised granules (urea/formaldehyde) and dried. If desired, it is also possible to apply a coating that allows the active ingredient to be released in metered amounts over a specific period of time (coated granules).

Preferred formulations have especially the following compositions:

(%=percent by weight)

Emulsifiable Concentrates:
  active ingredient mixture: 1 to 90%, preferably 5 to 20%
  surfactant: 1 to 30%, preferably 10 to 20%
  liquid carrier: 5 to 94%, preferably 70 to 85%

Dusts:
  active ingredient mixture: 0.1 to 10%, preferably 0.1 to 5%
  solid carrier: 99.9 to 90%, preferably 99.9 to 99%

Suspension Concentrates:
  active ingredient mixture: 5 to 75%, preferably 10 to 50%
  water 94 to 24%, preferably 88 to 30%
  surfactant: 1 to 40%, preferably 2 to 30%

Wettable Powders:
  active ingredient mixture: 0.5 to 90%, preferably 1 to 80%
  surfactant: 0.5 to 20%, preferably 1 to 15%
  solid carrier: 5 to 95%, preferably 15 to 90%

Granules:
  active ingredient mixture: 0.1 to 30%, preferably 0.1 to 15%
  solid carrier: 99.5 to 70%, preferably 97 to 85%

The following Examples further illustrate but do not limit the invention.

Formulation Examples for mixtures of ab) herbicide of formula I and co-herbicides under b), and safener under c) of formula 3.1 (% = percent by weight)

| F1. Emulsifiable concentrates | a) | b) | c) | d) |
|---|---|---|---|---|
| active ingredient mixture | 5% | 10% | 25% | 50% |
| calcium dodecylbenzenesulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| cyclohexanone | — | — | 10% | 20% |
| arom. hydrocarbon mixture $C_9$-$C_{12}$ | 85% | 78% | 55% | 16% |

Emulsions of any desired concentration can be obtained from such concentrates by dilution with water.

| F2. Solutions | a) | b) | c) | d) |
|---|---|---|---|---|
| active ingredient mixture | 5% | 10% | 50% | 90% |
| 1-methoxy-3-(3-methoxy-propoxy)-propane | — | 20% | 20% | — |
| polyethylene glycol MW 400 | 20% | 10% | — | — |
| N-methyl-2-pyrrolidone | — | — | 30% | 10% |
| arom. hydrocarbon mixture $C_9$-$C_{12}$ | 75% | 60% | — | — |

The solutions are suitable for use in the form of microdrops.

| F3. Wettable powders | a) | b) | c) | d) |
|---|---|---|---|---|
| active ingredient mixture | 5% | 25% | 50% | 80% |
| sodium lignosulfonate | 4% | — | 3% | — |
| sodium lauryl sulfate | 2% | 3% | — | 4% |
| sodium diisobutylnaphthalenesulfonate | — | 6% | 5% | 6% |
| octylphenol polyglycol ether (7-8 mol of ethylene oxide) | — | 1% | 2% | — |
| highly dispersed silicic acid | 1% | 3% | 5% | 10% |
| kaolin | 88% | 62% | 35% | — |

The active ingredient (or active ingredient mixture) is mixed thoroughly with the adjuvants and the mixture is thoroughly ground in a suitable mill, affording wettable powders which can be diluted with water to give suspensions of any desired concentration.

| F4. Coated granules | a) | b) | c) |
|---|---|---|---|
| active ingredient mixture | 0.1% | 5% | 15% |
| highly dispersed silicic acid | 0.9% | 2% | 2% |
| inorganic carrier (diameter 0.1-1 mm) e.g. $CaCO_3$ or $SiO_2$ | 99.0% | 93% | 83% |

The active ingredients (or active ingredient mixture) are dissolved in methylene chloride and applied to the carrier by spraying, and the solvent is then evaporated off in vacuo.

| F5. Coated granules | a) | b) | c) |
|---|---|---|---|
| active ingredient mixture | 0.1% | 5% | 15% |
| polyethylene glycol MW 200 | 1.0% | 2% | 3% |
| highly dispersed silicic acid | 0.9% | 1% | 2% |
| inorganic carrier (diameter 0.1-1 mm) e.g. $CaCO_3$ or $SiO_2$ | 98.0% | 92% | 80% |

The finely ground active ingredients (or the finely ground active ingredient mixture) are uniformly applied, in a mixer, to the carrier moistened with polyethylene glycol. Non-dusty coated granules are obtained in this manner.

| F6. Extruder granules | a) | b) | c) | d) |
|---|---|---|---|---|
| active ingredient mixture | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredients (or active ingredient mixture) are mixed and ground with the adjuvants, and the mixture is moistened with water. The mixture is extruded and then dried in a stream of air.

| F7. Dusts | a) | b) | c) |
|---|---|---|---|
| active ingredient mixture | 0.1% | 1% | 5% |
| talcum | 39.9% | 49% | 35% |
| kaolin | 60.0% | 50% | 60% |

Ready-to-use dusts are obtained by mixing the active ingredients (or active ingredient mixture) with the carriers and grinding the mixture in a suitable mill.

| F8. Suspension concentrates | a) | b) | c) | d) |
|---|---|---|---|---|
| active ingredient mixture | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredients (or the finely ground active ingredient mixture) are intimately mixed with the adjuvants, giving a suspension concentrate from which suspensions of any desired concentration can be obtained by dilution with water.

It is often more practical for the active ingredient ab) of formula I and the co-herbicides under b) and the safener under c) of formula 3.1 to be formulated separately and then to be brought together in the desired mixing ratio in the applicator in the form of a "tank mixture" in water shortly before application.

The ability of the safener of formula 3.1 to protect crop plants against the phytotoxic action ab) of the herbicide of formula I and the co-herbicides under b) is illustrated in the following Example.

BIOLOGICAL EXAMPLE

Safening Action

The test plants are grown in plastics pots under greenhouse conditions to the 1- to 4-leaf stage. At that stage, the herbicides alone and the mixtures of the herbicides with the test compound being tested as safener are applied to the test plants. The test compounds are applied in the form of an aqueous suspension prepared from a 25% suspension concentrate (Example F8, c)) with 500 litres of water/ha. 1 to 4 weeks after application, the phytotoxic action of the herbicides on the crop plants, e.g. rice, is evaluated using a percentage scale. 100% indicates that the test plant has died, 0% indicates no phytotoxic action. The mixtures according to the invention exhibit good selectively herbicidal action in this test.

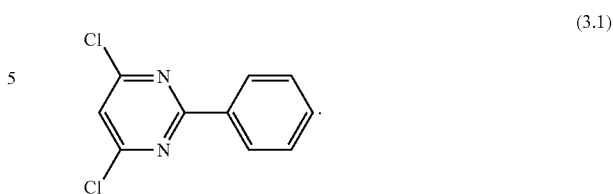

(3.1)

What is claimed is:

1. A synergistic herbicidal composition for the selective control of weeds and grasses which, in addition to comprising customary inert formulation adjuvants, comprises as active ingredient a mixture of
   a) a herbicidally effective amount of pretilachlor; and
   b) a synergistically effective amount of the co-herbicide prosulfocarb (656).

2. A selectively herbicidal composition which, in addition to comprising customary inert formulation adjuvants, comprises
   a) a synergistic herbicidal composition as defined in claim 1, and
   b) an amount, effective for crop safening, of the compound of formula 3.1.

3. A method of selectively controlling weeds and grasses in a crop of useful plants, which comprises treating the useful plants, seeds or cuttings thereof or the area of cultivation thereof with a herbicidally effective amount of a composition according to claim 2.

4. The herbicidal composition according to claim 1, wherein the herbicide under a) is present in a weight ratio of from 1:2000 to 2000:1 relative to the co-herbicide under b).

5. A method of selectively controlling undesired plant growth in crops of useful plants, which comprises treating the useful plants, seeds or cuttings thereof or the area of cultivation thereof, simultaneously or separately, with an amount, effective for herbicide synergy, of (a) the herbicide pretilachlor and (b) the co-herbicide prosulfocarb.

6. The method according to claim 5, wherein the crop plant is rice.

7. The method according to claim 5, wherein the crops of useful plants are treated with the mentioned composition at rates of application corresponding to a total amount of active ingredient of from 1 to 5000 g per hectare.

8. The method according to claim 3, wherein the rate of application of herbicides is from 1 to 5000 g/ha and the rate of application of the compound of formula 3.1 is from 1 to 1000 g/ha.

9. The method according to claim 3, wherein the crops of useful plants are rice.

* * * * *